(12) United States Patent
Fukumura et al.

(10) Patent No.: US 8,911,975 B2
(45) Date of Patent: Dec. 16, 2014

(54) METHOD FOR PRODUCING VIRUS VECTOR FOR GENE TRANSFER

(75) Inventors: Masayuki Fukumura, Mie (JP); Mitsuo Kawano, Mie (JP); Tetsuya Nosaka, Mie (JP); Junpei Ohtsuka, Mie (JP)

(73) Assignees: Mie University, Mie (JP); BioComo Inc., Mie (JP)

( * ) Notice: Subject to any disclaimer, the term of this patent is extended or adjusted under 35 U.S.C. 154(b) by 0 days.

(21) Appl. No.: 13/983,191

(22) PCT Filed: Feb. 8, 2012

(86) PCT No.: PCT/JP2012/000838
§ 371 (c)(1),
(2), (4) Date: Oct. 1, 2013

(87) PCT Pub. No.: WO2012/108195
PCT Pub. Date: Aug. 16, 2012

(65) Prior Publication Data
US 2014/0322760 A1  Oct. 30, 2014

(30) Foreign Application Priority Data

Feb. 8, 2011 (JP) ................................. 2011-025234

(51) Int. Cl.
C12N 15/64 (2006.01)
C12N 15/86 (2006.01)
C12N 7/04 (2006.01)
C12N 5/10 (2006.01)
C12N 5/16 (2006.01)

(52) U.S. Cl.
CPC ..................................... *C12N 15/64* (2013.01)
USPC ..... 435/91.4; 435/69.1; 435/70.1; 435/235.1; 435/236; 435/239; 435/364

(58) Field of Classification Search
CPC ............ A61K 35/76; A61K 2039/543; C12N 2760/18711; C12N 2760/18741; C12N 2760/18743; C12N 2760/18751; C12N 2760/18752; C12N 2760/18762
See application file for complete search history.

(56) References Cited

U.S. PATENT DOCUMENTS

2003/0170885 A1  9/2003  Imler et al.
2009/0041725 A1  2/2009  Neubert et al.
2012/0219582 A1  8/2012  Yasutomi et al.

FOREIGN PATENT DOCUMENTS

| CN | 1646684 A | 7/2005 |
|---|---|---|
| CN | 1856575 A | 11/2006 |
| CN | 1871355 A | 11/2006 |
| EP | 1186667 A1 | 3/2002 |
| JP | 2008-074749 A | 4/2008 |
| WO | 94/28152 A1 | 12/1994 |
| WO | 00/70070 A1 | 11/2000 |
| WO | 0183794 A2 | 11/2001 |
| WO | 03072720 A2 | 9/2003 |
| WO | 2004/027037 A2 | 4/2004 |
| WO | 2004113517 A2 | 12/2004 |
| WO | 2006/084746 A1 | 8/2006 |
| WO | 2007/120120 A2 | 10/2007 |
| WO | 2011/052771 A1 | 5/2011 |

OTHER PUBLICATIONS

Kelly J. Henrickson, Parainfluenza viruses, Clinical Microboiology Reviews, 2003, vol. 16, No. 2, p. 242-264.
Qizhi Yao, et al., Association of the parainfluenza virus fusion and hemagglutinin-neuraminidase glycoproteins on cell surfaces., J.Virol., 1997, vol. 71, No. 1, p. 650-656.
Kaoru Shimokata, et al., Influence of trypsin on the infectivity and biological properties of parainfluenza type 2 (croup-associated) virus in vero cells., J. Gen. Virol., 1980, vol. 48, No. 2, p. 407-410.
International Search Report for PCT/JP2012/000838; dated Mar. 19, 2012.
Chinese Office Action dated May 27, 2014 for Chinese Application No. 201280008073.4.
Kawano, et al. "Complete Nucleotide Sequence of the Matrix Gene of Human Parainfluenza Type 2 Virus and Expression of the M Protein in Bacteria", Virology 179, pp. 857-861 (1990).

*Primary Examiner* — Louise Humphrey
(74) *Attorney, Agent, or Firm* — Pearne & Gordon LLP

(57) ABSTRACT

The present invention discloses a cell system, as a host cell to be infected with an F gene-deficient virus, which can constitutively and stably express the F protein, and a method for producing an F gene-deficient virus by utilizing the cell. A non-proliferative human parainfluenza type 2 virus vector is produced by co-culturing an F gene-deficient human parainfluenza type 2 virus with a Vero cell having the F gene of human parainfluenza type 2 virus in such a manner that the F gene is non-inducibly expressed, and isolating viral particles from a culture supernatant.

3 Claims, 5 Drawing Sheets

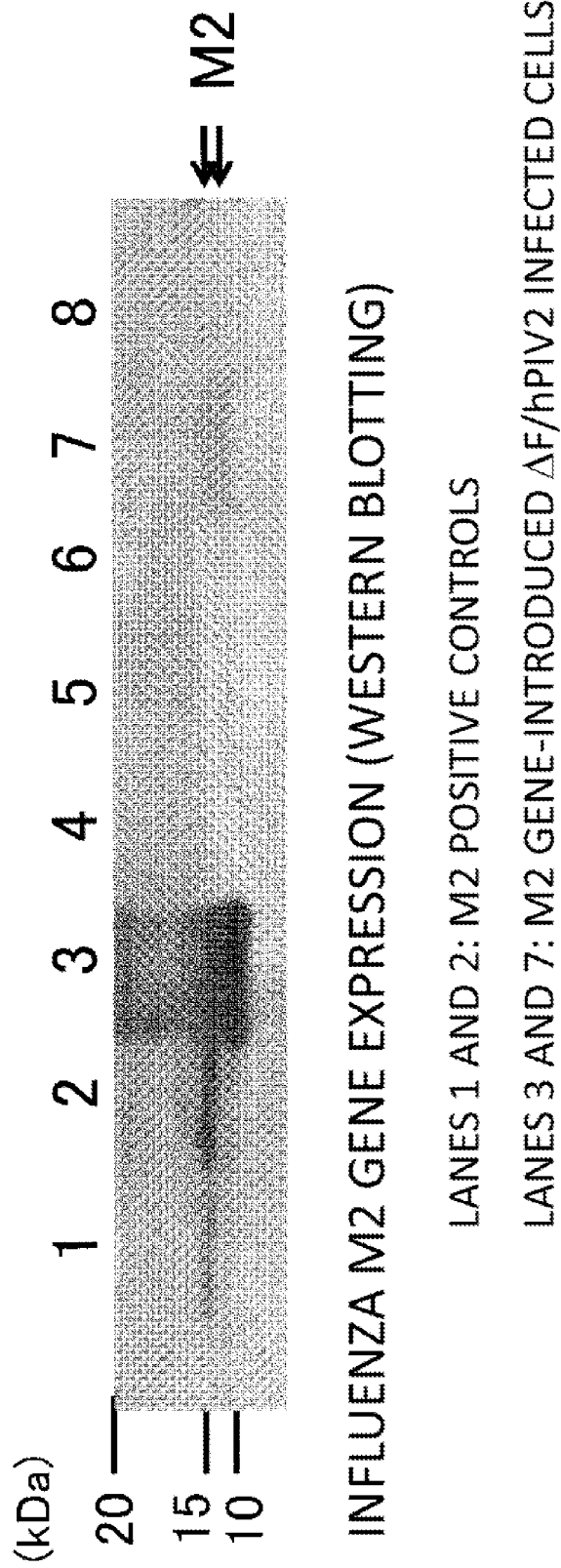

METHOD FOR PRODUCING VIRUS VECTOR FOR GENE TRANSFER

TECHNICAL FIELD

1. Related Application

The present application claims benefit of priority to Japanese Patent Application No. 2011-025234 filed on Feb. 8, 2011, the content of which is incorporated herein by reference.

2. Technical Field

The present invention relates to a method for producing a virus vector for gene transfer.

BACKGROUND ART

Human parainfluenza type 2 virus (hPIV2) infects human respiratory mucosa and can induce mucosal immunity, and therefore is expected to find application as a vaccine vector. In order to put this vector to practical use, the virus vector is required to have an ability to infect human cells and not to generate transmissible viruses in the human body after infection (such a vector is referred to as a non-proliferative vector). Thus a system is required which can primarily infect cells or tissue but does not produce transmissible viruses in the infected cells or tissue so that it does not cause recurrent infections. The procedure for construction of such a system generally includes partially deleting a gene on a viral genome, preparing cells expressing a product encoded by the deleted gene, and complementing in trans the defective virus in the cells with the product encoded by the deleted gene to prepare a non-proliferative vector. This system has been introduced to DNA viruses such as adenoviruses (e.g. WO 94/28152) and RNA viruses such as retroviruses (e.g. WO 2006/084746). For viruses of *Paramyxoviridae* to which human parainfluenza type 2 virus belongs, a Sendai virus vector defective in the F gene and the like has been proposed (WO 2000/070070). It has also been reported that a vaccine for the prevention of onset of tuberculosis, which utilizes a non-proliferative recombinant vector derived from human parainfluenza type 2 virus by incorporating an a antigen (Ag85B) gene from typical mycobacteria such as *Mycobacterium kansasii* or *Mycobacterium bovis* BCG (PCT/JP 2010/069435), has a high suppressing effect of *Mycobacterium tuberculosis* proliferation.

F gene-deficient human parainfluenza type 2 virus does not contain, in itself, the Fusion protein (hereinafter referred to as "F protein") of human parainfluenza type 2 virus which is required for, during viral replication and transcription after invasion into a host cell, fusing a viral envelope with a cell membrane and introducing a viral nucleocapsid into the host cell, and thus cannot form replication competent viral particles. Therefore the preparation of a non-proliferative human parainfluenza type 2 virus vector which is defective in the F gene on the genome but contains the F protein on a vector envelope includes generating cells expressing the F protein of the virus, culturing the defective virus on the cells in order to retain the F protein on the viral envelope in the presence of the F protein complemented in trans by the cells and thereby constructing infectious viral particles. The human parainfluenza type 2 virus particles collected from the culture supernatant prepared according to the above replication system contain a genome lacking the F gene. Incorporating therapeutic genes or genes encoding vaccine antigens into the F gene-defective human parainfluenza type 2 virus vector may provide viral particles useful as medicaments.

Because viruses generally include membrane proteins which are cytotoxic, it has been conventionally necessary to suppress expression of the viral F gene and the like at normal times by establishing a cell line after introducing a vector which is designed to express the F gene and the like under the control of an inducible promoter and to induce the expression of the F gene and the like only when the virus is reconstituted after infecting helper cells which express the F gene and the like. In the above document pertaining to the Sendai virus vector (WO 2000/070070), for example, a system is used in which the F gene of Sendai virus is not expressed during proliferation of host cells by using the Cre-loxP inducible system and the expression thereof is induced upon infection of the virus to the cells by addition of an adenovirus.

However, the step of preparation and addition of an adenoviruses makes commercial production of the virus vector complicated. There is also a problem in that the medicament manufacturing control step becomes complicated because the gene introducing efficacy by an adenovirus is not constant. Further there is a problem in that during actual production of the virus vector with the membrane protein expression inducible system by culturing cells and replicating viral particles, the viral replication capacity decreases with an increase in the number of passages of the host cells due to toxicity of the expressed membrane protein, such that the cells lose the production ability of the virus after about 5 passages.

Therefore there is a need to obtain, as a cell which can express a gene encoding a membrane protein and the like that is defective in a virus and allows replication of the defective virus vector, a cell system which can constitutively and stably express the protein. There is also a need for a host cell system which has such robustness that the properties thereof are stable after subculturing.

The references cited in the present specification are shown below. The contents of these references are incorporated herein by reference in their entirety. However it does not intend to admit that any of these references is available as "Prior Art" to the present specification.

Patent Document 1: WO 94/28152
Patent Document 2: WO 2006/084746
Patent Document 3: WO 2000/070070
Patent Document 4: PCT/JP 2010/069435

DISCLOSURE OF INVENTION

An object of the present invention is to provide, as a cell for proliferating a virus deficient in the F gene of human parainfluenza type 2 virus, a cell system which can constitutively and stably express the F protein of human parainfluenza type 2 virus, and to provide a method for producing an F gene-deficient human parainfluenza type 2 virus by utilizing the cell.

The present inventors have found that Vero cells have excellent properties to be used as packaging cells that can be infected with a virus deficient in the F gene of human parainfluenza type 2 virus and produce viral particles. It has been found surprisingly that Vero cells have high tolerance to the F protein of human parainfluenza type 2 virus, do not express interferons, can stably proliferate under constitutive expression of the F gene of human parainfluenza type 2 virus and can effectively produce viral particles.

Thus the present invention provides a method for producing a non-proliferative human parainfluenza type 2 virus vector. The method includes the steps of co-culturing an F gene-deficient human parainfluenza type 2 virus with a Vero cell having the F gene of human parainfluenza type 2 virus in such a manner that the F gene is non-inducibly expressed, and isolating viral particles from a culture supernatant.

In a preferred embodiment of the method of the present invention, the F gene-deficient human parainfluenza type 2 virus has a gene into which a vaccine or therapeutic gene has been incorporated.

In another aspect, the present invention provides a Vero cell having the F gene of human parainfluenza type 2 virus in such a manner that the F gene is non-inducibly expressed.

The method of the present invention allows effective and stable production of non-proliferative human parainfluenza type 2 virus vectors.

BRIEF DESCRIPTION OF THE DRAWINGS

FIG. 5 shows a western blotting confirming expression of the M2 protein by an M2 gene-harboring F gene-deficient hPIV2.

BEST MODE FOR CARRYING OUT THE INVENTION

The present invention provides a method for replicating an F gene-deficient human parainfluenza type 2 virus by using Vero cells having the F gene of human parainfluenza type 2 virus in such a manner that the F gene is non-inducibly expressed.

Figure 1:
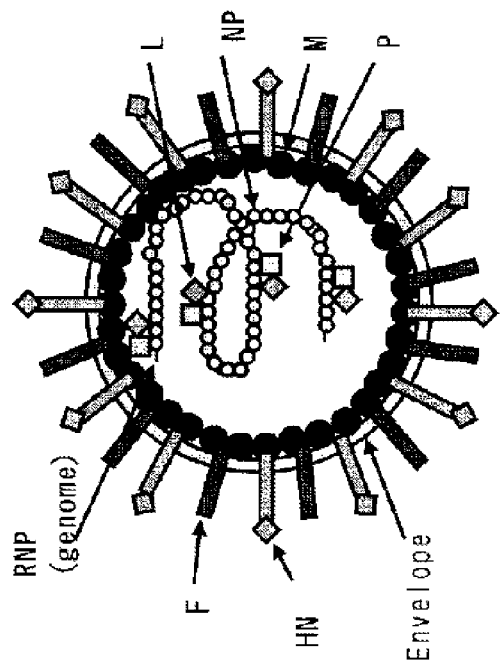
FIG. 1 shows a particle structure and a genome of human parainfluenza type 2 virus.
Figure 1:
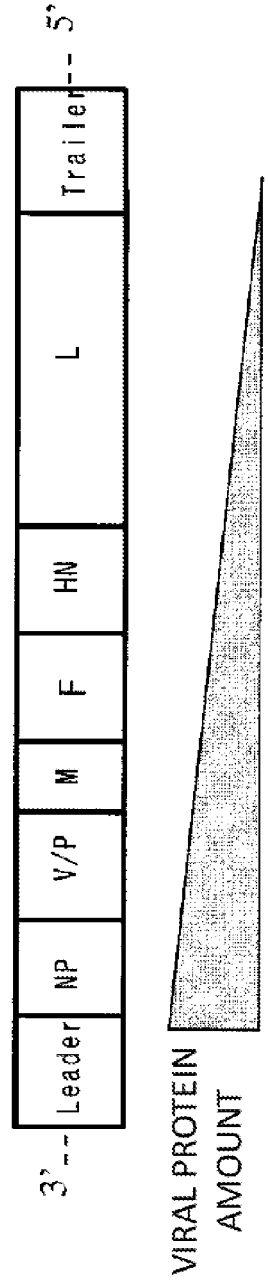

Human parainfluenza type 2 virus belongs to *Paramyxoviridae* and has a genome which is a monocistronic single-stranded negative RNA of about 15,000 bases. FIG. 1 shows the fundamental particle structure of human parainfluenza type 2 virus (hPIV2). The nucleic acid binds to a nucleocapsid protein (NP) to form a helically symmetric ribonucleoside-protein complex (nucleocapsid; RNP). Among the proteins encoded by the viral genome, the NP protein, the P (phospho) protein and the L (large) protein are necessary for formation of the RNP. The F (fusion) protein and the HN (hemagglutinin-neuraminidase) protein are envelope proteins and important for cell infection. The M (matrix) protein is a membrane protein which supports the envelope structure.

Human parainfluenza type 2 virus is an RNA virus replicating in the cytoplasm of the infected cells and thus the gene of the virus is not incorporated into chromosomes of the host cells. Based on the facts that it is known that the virus infects human respiratory mucosa and induces mucosal immunity by inducible expression of IgA and that severe infection therewith in adults has not been reported to date, the virus is believed to be significantly useful as a vaccine or therapeutic viral vector.

Human parainfluenza type 2 virus modified to express the NP, P and L proteins but not the F protein can infect primarily a cell; however it cannot produce infectious viral particles in the cell. Therefore it has such an advantage that it is highly safe as a therapeutic or vaccine viral vector.

The Vero cell expressing the F protein of human parainfluenza type 2 virus of the present invention is a host cell useful for production of F gene-deficient viral particles by replicating the virus deficient in the F gene of the viral genome.

"Vero cells" are cultured cells derived from African green monkey kidney epithelium which are characterized by the absence of interferon production and constitute a cell line which is widely used worldwide mainly for virus infection studies and vaccine production. In the present invention, any commercially available Vero cells may be used.

The "F gene" is a gene encoding the F protein of human parainfluenza type 2 virus. This term is used herein to mean not only viral genomic RNA but also both DNA and RNA having corresponding sequences or complementary sequences thereof.

The term "non-inducibly expressed" means that the expression is designed to proceed without requiring an inducible expression system and that the expression proceeds without any induction operation. The inducible expression system refers to a system based on a combination of host cell/vector and culture conditions which is designed so as not to allow expression without an induction operation or with a suppression operation but to allow expression only with the induction operation or with elimination of the suppression operation. Many inducible expression systems are known in the art. Non-inducible expression means expression which proceeds without an induction operation or elimination of a suppression operation. The non-inducible expression typically is constitutive expression. The "non-inducible" expression as used herein, however, also encompasses expression which may be suppressed in a particular phase during cell division or cell cycle and expression which may be suppressed according to culture conditions such as culture temperature, composition of a media or cell density.

The F protein-expressing Vero cell of the present invention is produced as follows: first a recombinant plasmid vector having the F gene and a marker (e.g. drug resistance) is prepared and is used for transfection of Vero cells. The sequence of the F gene is already known, so that the recombinant plasmid vector can be readily produced by incorporating the F gene into a commercially available appropriate plasmid vector. Transfection can be performed according to a conventional method using various commercially available transfection reagents or by electroporation. Next, transformants are identified by utilizing the marker, which are then isolated and subjected to cell expansion. Expression of the F protein in the transformed Vero cells can be analyzed by immunostaining using an antibody; analysis of expression on protein level by western blotting as described in examples hereinbelow; or analysis of expression on RNA level by RT-PCR and the like. Expression of the F protein may alternatively be confirmed by observing formation of syncytium during cell fusion of infected cells. The formation of syncytium refers to the formation of giant cells containing a plurality of cell nuclei due to co-expression of the F protein and another viral membrane protein, a receptor-binding protein HN, in a single cell causing fusion of adjacent cells. When Vero cells to which the F gene is expected to be incorporated are transfected with a plasmid containing the HN gene and the formation of syncytium is confirmed, the cells are confirmed to functionally express the F gene. Accordingly desirable recombinant Vero cells expressing the F gene can be cloned.

In another aspect of the present invention, a method for producing an F gene-deficient non-proliferative human parainfluenza type 2 virus vector is provided. The method comprises the steps of co-culturing an F gene-deficient human parainfluenza type 2 virus with the Vero cell of the present invention having the F gene of human parainfluenza type 2 virus in such a manner that the F gene is non-inducibly expressed; and isolating viral particles from a culture supernatant.

The term "virus vector" means a viral particle in which a gene to be expressed in an infected cell and a viral genomic gene are packaged.

The viral genomic gene lacking the F gene can be constructed from a plasmid containing an antisense cDNA corresponding to the whole genomic gene of hPIV2 using conventional gene recombination technique by deleting a whole or partial F gene or by introducing a stop codon mutation within the F gene. It is preferable that the whole F gene is deleted in order to prevent the virus vector administered to a subject from re-acquiring the function of the F gene due to mutation. The non-proliferative virus vector according to the present invention is preferably designed to include a cloning site for incorporating various therapeutic genes.

In order to produce F gene-deficient viral particles from the viral genomic gene lacking the F gene, a plasmid constructed so as to express the viral genomic gene lacking the F gene under the control of a T7 promoter is used for transfection of cells expressing a T7 RNA polymerase together with four vectors expressing the F protein and a polymerase unit (NP protein, P protein and L protein) of hPIV2, or for transfection of Vero cells expressing the F gene together with four vectors expressing the T7 RNA polymerase and a polymerase unit (NP protein, P protein and L protein) of hPIV2. The infected cells are cultured for 3 to 6 days and F gene-deficient viral particles can be collected from a culture supernatant.

Infection of the thus obtained F gene-deficient viral particles with the F gene-expressing Vero cells of the present invention allows production of infectious viral particles which are proliferated in the cells, are F gene-deficient viral particles and have the F-protein on the viral envelope.

In a preferred embodiment of the present invention, the virus vector based on the F gene-deficient human parainfluenza type 2 virus is incorporated with a therapeutic or vaccine gene, so that infection of the non-proliferative virus vector obtained by the present method with a target cell allows introduction of the therapeutic gene into the target cell. The therapeutic gene is a gene to be expressed in an infected cell and examples thereof may include a gene encoding a protein derived from mammals including human or a part thereof; a gene encoding a tumor antigen or a part thereof; a gene derived from bacteria or viruses; a gene encoding a therapeutic antibody or a part thereof; and a fragment thereof; and a gene which is obtained by introducing a mutation into the gene described above. The virus vector containing the gene derived from bacteria or viruses or a fragment thereof is useful as a vaccine. The therapeutic gene can be incorporated into the human parainfluenza type 2 virus gene according to a conventional method using conventional recombinant DNA techniques and reverse genetics techniques.

The virus vector produced according to the present invention can be typically administered to mammalian cells including human cells in the form of a spray. The spray can be prepared according to a conventional method. For example, the spray may be prepared by optionally concentrating a culture supernatant containing the virus vector, suspending the same with an appropriate carrier or excipient into a buffer such as PBS or saline, optionally sterilizing the same through a filter and the like, and then charging the same in a sterilized container. The spray may optionally contain a stabilizer, a preservative and the like. The thus obtained expression vector may be administered to a subject by inhalation.

The embodiments described with the expression "comprising" as used herein encompass the embodiments described with the expression "essentially consisting of" and the embodiments described with the expression "consisting of".

The contents of all patents and references explicitly cited herein are incorporated herein by reference in their entirety.

EXAMPLES

The present invention is hereinafter further illustrated by way of examples which do not limit the present invention.

Example 1

Preparation of F Gene-Expressing Vero Cells

To a plasmid harboring a neomycin resistant gene (Neo) as well as an avian β-actin promoter sequence and a rabbit β-globin polyA sequence was introduced the F gene excised from the hPIV2 genomic gene to construct a plasmid pCXN2-F. A control plasmid pCAL-F was used which was constructed so as to express the F gene through the Cre-loxP inducible system. Vero cells were transfected with these plasmids using Nucleofector from Amaxa.

The transfected cells were cultured in a medium containing neomycin (1 mg/ml) in order to screen the cells for neomycin drug resistance. Twenty (20) and 27 drug resistant colonies were isolated from the cells to which pCXN2-F was introduced and the cells to which pCAL-F was introduced, respectively, and were examined for the expression of the F gene. The cells to which the plasmid pCAL-F was used were infected with Cre gene-harboring adenovirus in order to remove the unnecessary gene fragment at the loxP sequences and induce F gene expression.

Next, formation of syncytium was examined. A plasmid SRα-HN which harbors the HN gene was prepared and used for transfection of the obtained neomycin resistant Vero cells using Nucleofector. The cells after 1 or 2 days were observed under microscopy for formation of syncytium and the cells forming syncytium were selected as F gene-expressing cells in this secondary selection. Among 20 clones isolated from the cells to which pCXN2-F was introduced, 12 clones showed the ability to form syncytium.

Figure 2:
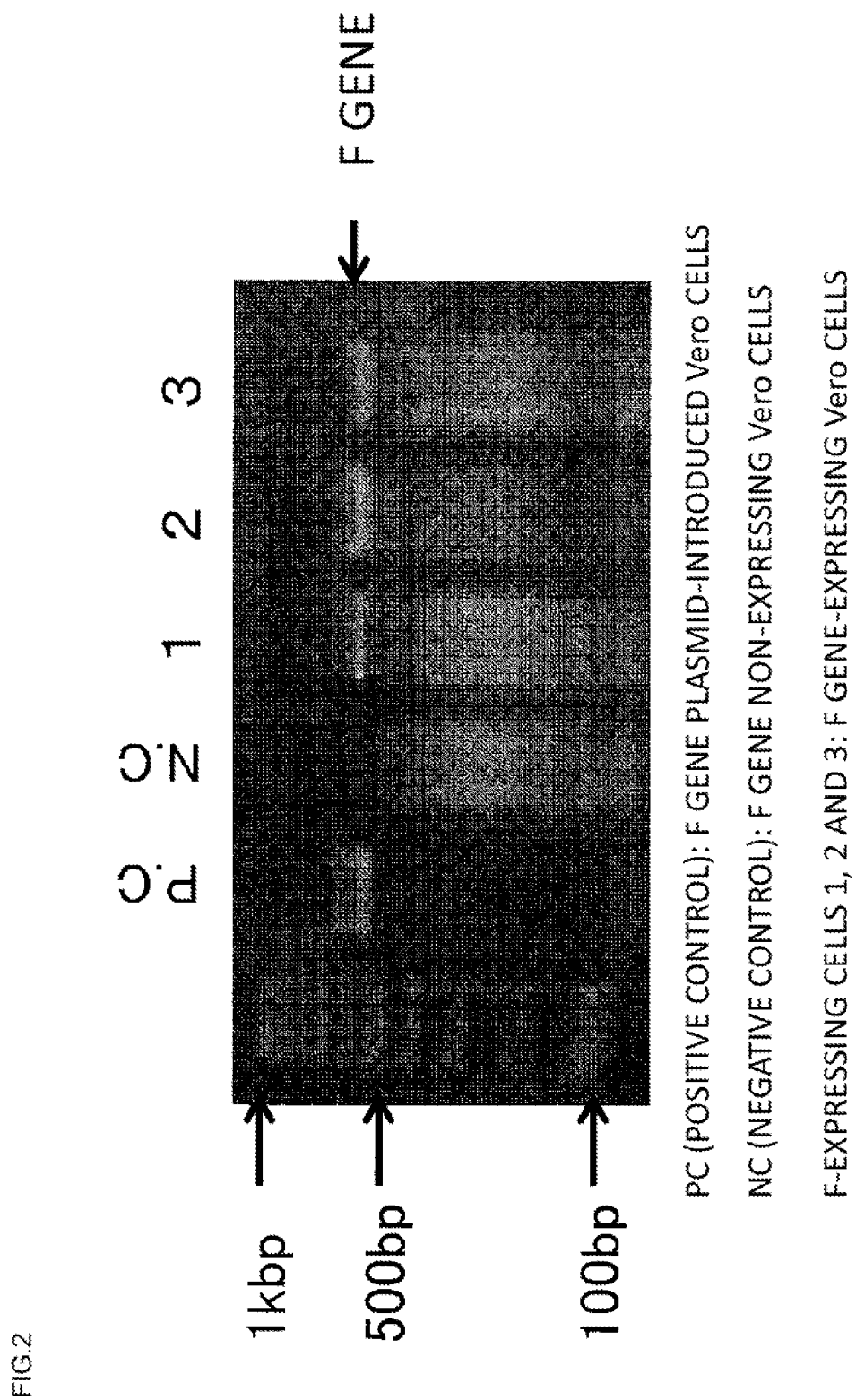
FIG. 2 is the confirmation of expression of the F gene in F gene-expressing Vero cells after a prolonged culture (about one year) which shows the retention of the F gene expression.

Expression of the F gene at RNA level was then measured by RT-PCR. As a result, among 20 clones isolated from the cells to which pCXN2-F was introduced, 12 clones showed the ability to form syncytium among which 9 clones were positive in RT-PCR. Among 27 clones isolated from the cells to which pCAL-F was introduced, 9 clones showed the ability to form syncytium among which 7 clones were positive in RT-PCR. Vero cells ($2 \times 10^6$) to which the F gene was introduced through pCXN2-F and cultured for one year were subjected to One-Step RT-PCR (QIAGEN). The primers for the PCR were designed so as to obtain a PCR amplification product around 550 bp when the F gene-deficient viral genome was present. As a result, bands of PCR amplification products around 550 bp were observed in PCR for different three clones, which further confirmed that the F gene remained to be expressed (FIG. 2). Thus the Vero cells constitutively expressing the F gene could be obtained at an efficiency equivalent to the Vero cells inducibly expressing the F gene, and the expression was stable for a prolonged period of time. This indicates that the Vero cells have high tolerance to the F protein and can stably proliferate even when the F gene is constitutively expressed for a prolonged period of time.

Figure 3:
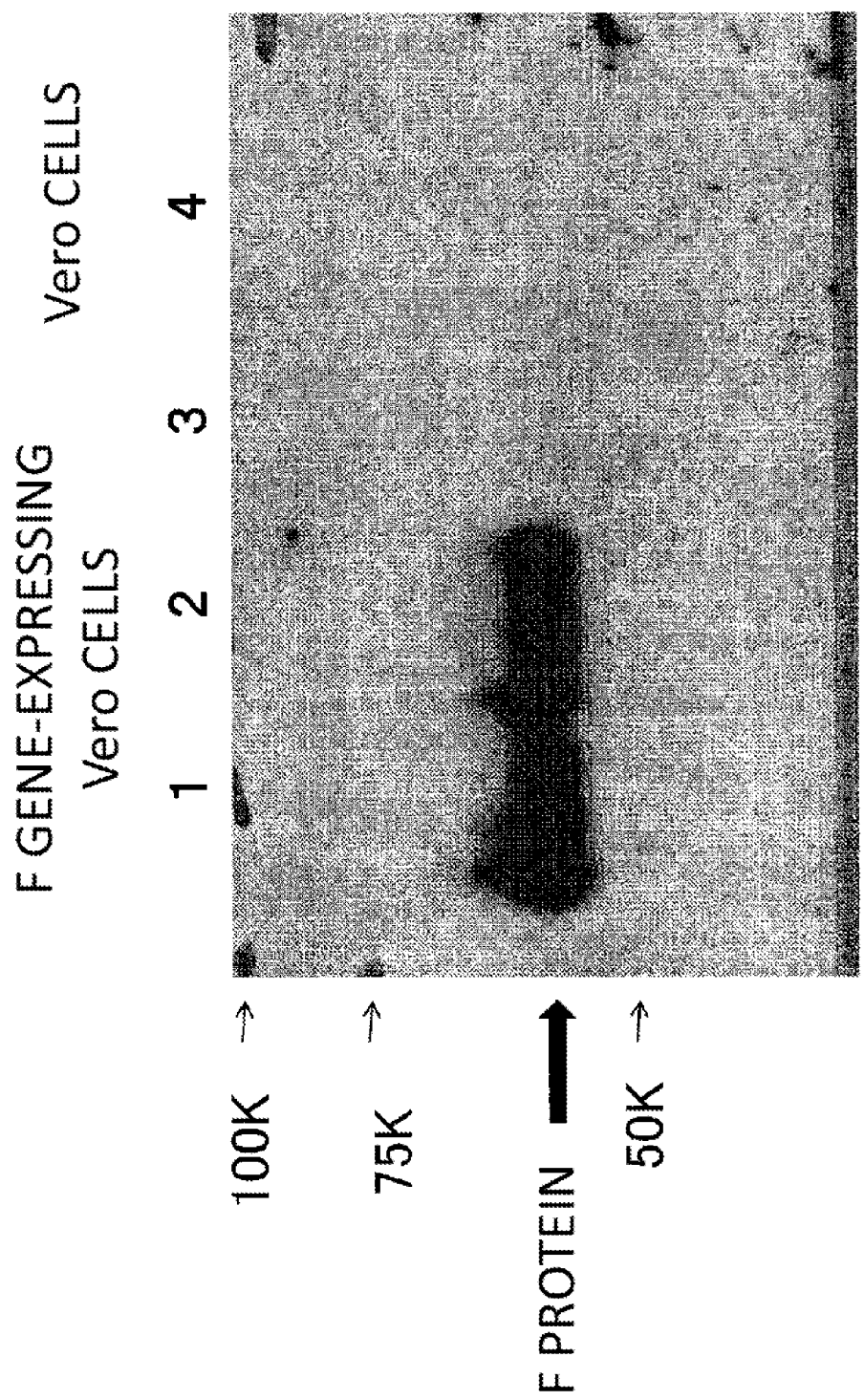
FIG. 3 shows a western blotting confirming expression of the F protein in F gene-introduced Vero cells.

Expression of the F protein was then examined in the F gene-expressing Vero cells. All proteins on the cell membrane were biotinylated by using 1 ml of 0.03% Sulfo-NHS-LC- Biotin solution on 9.5×10⁵ F gene-expressing Vero cells and 500 μl of cell lysate was prepared under a mild condition. The cell lysate (300 μl) was subjected to immunoprecipitation using 80 μl of an F protein specific antibody in order to selectively recover and concentrate only the F protein by binding to the antibody. The whole amount of the sample was subjected to SDS-PAGE and transferred to a PVDF membrane. The F protein at this stage was already biotinylated, so that it formed an avidin-biotin complex by an avidin-biotin complex method. By using horseradish peroxidase (HRP) conjugated to avidin, the biotinylated F protein was detected by light emission from HRP after reaction with an ECL reagent (FIG. 3).

Example 2

Construction of F Gene-Deficient Antisense hPIV2 Genome

Figure 4:
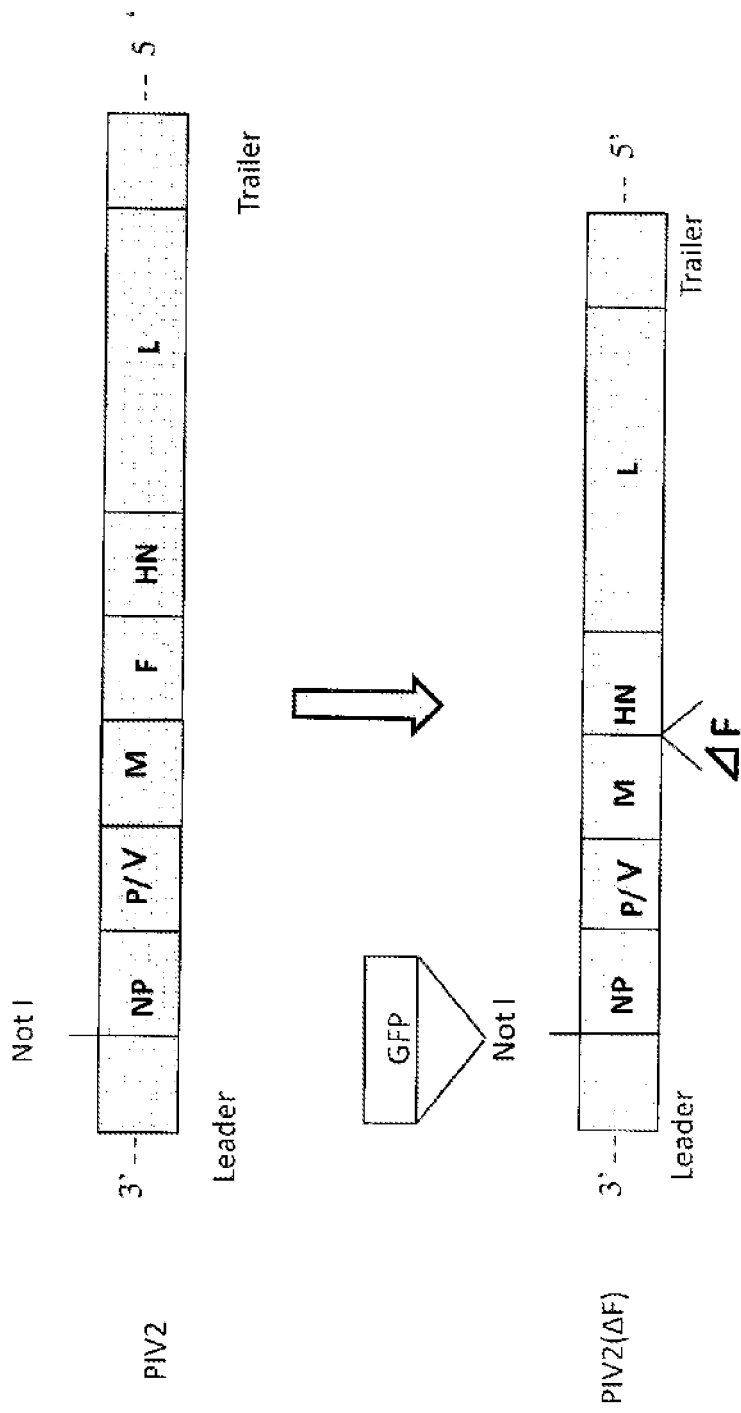
FIG. 4 shows a partial structure of a plasmid containing an antisense genomic cDNA of an F gene-deficient human parainfluenza type 2 virus and the GFP gene.

A plasmid (hPIV2-ΔF-GFP) was prepared from a plasmid containing an antisense cDNA corresponding to the whole genomic gene of hPIV2 downstream of a T7 promoter by completely deleting the sequence containing the total F gene encoding region and incorporating a GFP (green fluorescence protein) gene at a Not I restriction site (FIG. 4). The construction was performed by multi-step PCR using primers which were designed based on the sequences upstream and downstream of the F gene; a GFP gene fragment excised from a commercially available GFP-containing vector; and the plasmid containing the hPIV2 genomic gene as a template.

Example 3

Recovery of F Gene-Deficient Viral Particles Using F-Expressing Vero Cells

Cells expressing a T7 RNA polymerase were transfected with the plasmid (hPIV2-ΔF-GFP) prepared in Example 2 using Lipofectamine or FUGENE 6 as a transfection reagent. At the same time, 4 vectors expressing the F protein and a polymerase unit (NP protein, P protein and L protein) of hPIV2 were also used for co-transfection.

The cells were cultured for 3 days and a supernatant was collected which was used for infection of the F gene-expressing Vero cells or normal Vero cells without expression of the F gene. After 6 days of the infection, the cells were examined for GFP fluorescence. GFP fluorescence was observed for whole F gene-expressing Vero cells while the number of normal Vero cells which emitted GFP fluorescence was far less than that of the F gene-expressing Vero cells.

The culture supernatant of the F gene-expressing Vero cells emitting GFP fluorescence was collected and used for infection of distinct F gene-expressing Vero cells on a plate of which supernatant was then collected. These procedures were repeated for three times prior to centrifugation of 1.5 ml of the supernatant at 1,000×g for 1 minute to remove the residue. The supernatant was then centrifuged at 20,000×g for 30 minutes, of which a supernatant was discarded and a precipitate was suspended in 20 μl of RNase-free water. The suspension (0.5 μl) was subjected to One-Step RT-PCR (QIAGEN). The primers for PCR were designed so as to result the band of about 400 bp when the F gene-deficient viral genome was present and the band of about 500 bp when the GFP gene was inserted. As a result, the bands of PCR amplification products at about 400 bp and about 500 bp were observed in the respective PCR reactions. Thus it suggested that F gene-deficient PIV2 virus was recovered.

The thus obtained culture supernatant of the GFP-expressing F gene-expressing Vero cells were passed through a 0.45-μm filter to remove the residue. The culture supernatant was subjected to 10-fold serial dilution and used for infection of Vero cells without F gene expression. After three days, cells were examined for GFP fluorescence. As a result, cells emitting GFP fluorescence were observed and the number of GFP positive cells was decreased proportionally to the dilution factor. Thus it was confirmed that the culture supernatant of the F gene-expressing Vero cells contained the F gene-deficient hPIV2 virus which infected the Vero cells without F gene expression. The culture supernatant of the Vero cells without F gene expression did not provide infectious viral particles.

Infection of mouse NIH-3T3 cells with the GFP gene-harboring F gene-deficient hPIV2 virus resulted in the GFP positive NIH-3T3 cells. However the efficiency of infection was lower than Vero cells.

Example 4

Preparation of F Gene-Deficient PIV2 Virus Expressing M2 Protein of Influenza Virus In the same manner as Example 2, a plasmid (hPIV2-ΔF-M2) was constructed by incorporating, at a Not I restriction site of the F gene-deficient antisense hPIV2 genome, a gene of an M2 protein (M2 ion channel) which exists on a lipid layer membrane of influenza virus. Cells expressing a T7 RNA polymerase were transfected with the plasmid (hPIV2-ΔF-M2) using Lipofectamine or FUGENE 6 as a transfection reagent in the same manner as Example 3. At the same time, 4 vectors expressing the F protein and a polymerase unit (NP protein, P protein and L protein) of hPIV2 were also used for co-transfection. The virus was recovered in the same manner as Example 3 and M2 gene-harboring F gene-deficient hPIV2 was used for infection of the F gene-expressing Vero cells (2×10⁶). The cells were collected after 2 days and subjected to western blotting using an M2 antibody. As a result, expression of M2 was confirmed (FIG. 5). Thus it was confirmed that the F gene-deficient PIV2 virus could be also recovered when the gene other than GFP was used.

Based on the above results, it was found that the use of the F gene-expressing Vero cells allowed recovery of the F gene-deficient non-proliferative hPIV2 virus and that this virus can proliferate only in F gene-expressing cells and can primarily infect the cells without F gene expression without producing infectious viruses.

INDUSTRIAL APPLICABILITY

The present invention is useful for production of virus vectors for gene therapy.

The invention claimed is:
1. A method for producing a non-proliferative human parainfluenza type 2 virus vector, comprising the steps of:
   co-culturing an F gene-deficient human parainfluenza type 2 virus with a Vero cell non-inducibly expressing the F gene of human parainfluenza type 2 virus, and isolating viral particles from a culture supernatant.
2. The method according to claim 1, wherein the F gene-deficient human parainfluenza type 2 virus comprises a vaccine or therapeutic gene.
3. An isolated Vero cell that is non-inducibly expressing the F gene of human parainfluenza type 2 virus.

* * * * *